United States Patent
Nilsson et al.

(12) 
(10) Patent No.: US 6,231,733 B1
(45) Date of Patent: *May 15, 2001

(54) IMMOBILIZED CARBOHYDRATE BIOSENSOR

(76) Inventors: Kurt Nilsson, Andjaktsv. 6, S-226 53, Lund; Carl-Fredrik Mandenius, Strömkarlsv. 36, S-141 42, Huddinge, both of (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/356,229

(22) Filed: Dec. 19, 1994

Related U.S. Application Data

(63) Continuation of application No. PCT/SE94/00343, filed on Apr. 18, 1994, now abandoned.

(30) Foreign Application Priority Data

Apr. 17, 1993 (SE) .................................................. 9301270

(51) Int. Cl.$^7$ .................................................. G01N 27/26
(52) U.S. Cl. .......................... 204/400; 204/403; 356/445; 422/68.1; 422/82.01; 422/82.05; 422/82.12; 435/5; 435/7.1; 435/7.2; 435/7.32; 435/7.8; 436/501; 436/164; 436/169; 436/805; 436/806; 436/827

(58) Field of Search ..................................... 204/403, 400; 356/445; 422/68.1, 82.01, 82.05, 82.12; 435/5, 7.1, 7.2, 7.32, 7.8; 436/501, 164, 169, 805, 806, 827, 528, 5.29, 5.97

(56) References Cited

U.S. PATENT DOCUMENTS

| | | |
|---|---|---|
| 4,415,665 | 11/1983 | Mosbach et al. . |
| 4,918,009 | 4/1990 | Nilsson . |
| 4,980,278 | 12/1990 | Yamada . |
| 5,246,840 | 9/1993 | Nilsson . |
| 5,372,937 | 12/1994 | Nilsson . |
| 5,405,752 | 4/1995 | Nilsson ............................. 435/7.94 |

FOREIGN PATENT DOCUMENTS

| | | |
|---|---|---|
| 3617763 | 8/1989 | (DE) . |
| 0215669 | 3/1987 | (EP) . |
| 90/01166 | 2/1990 | (WO) . |
| 92/12995 | 8/1992 | (WO) . |
| WO94/00763 | 1/1994 | (WO) . |

*Primary Examiner*—Christopher L. Chin
*Assistant Examiner*—Bao-Thuy L. Nguyen
(74) *Attorney, Agent, or Firm*—Smith, Gambrell & Russell, L.L.P.

(57) ABSTRACT

A biosensor in which a carbohydrate or a derivative of a carbohydrate is used to generate a detectable signal by way of the specific binding to a protein, a virus or a cell.

58 Claims, No Drawings

IMMOBILIZED CARBOHYDRATE BIOSENSOR

This is a continuation of international application PCT/SE94/00343, filed Apr. 8, 1994, which designated the United States and is now abandoned.

The present invention relates to a biosensor in which a carbohydrate or a derivative thereof is used to generate a detectable signal via the specific binding of a protein, a virus or a cell.

BACKGROUND

Biosensors are characterised by a physical or chemical signal transducer, which response is activated by a specific interaction between a biochemical structure (which directly or indirectly has been bound to the transducer) and one or several analytes.

Biosensors are used to detect the analyte/analytes and in certain cases also for quantification of the analyte/analytes.

The advantages of the biosensor are that a physical or chemical transducer has been made specific so that a general physical or chemical parameter (e.g. temperature, pH, optical density) can be used for the detection of one specific substance in a complex mixture of non-specific substances.

The limitations of the biosensor are the specificity of the biochemical structure bound to the transducer, the range of specificity and stability, and, that the transducer signal has to be made independent of the background changes in the parameter that the transducer is measuring. In Methods of Enzymology, volume 137, several articles are describing different aspects of biosensors.

DEFINITIONS

Biosensor—physical or chemical signal transducer, e.g. photometer, chemical electrode, temperature or pressure signal transducer, which directly or indirectly has been connected with a biochemical structure. In previous biosensors one has preferentially used an enzyme, a specific protein or antibody as the biochemical structure and in this way the biosensors have been given the property of being able to detect substances which specifically bind to the biochemical structure in a qualitative or quantitative way.

Reflection measurement—measurement of the intensity of light reflected from a surface where the properties of the surface influences the reflection, e.g. biomolecules which change the refraction index of the surface.

Polarisation measurement—measurement of the polarisation of polarised light, usually as the angle of polarisation, which is depending on the binding of biomolecules, virus or cells.

Surface plasmon spectroscopy—optical physical measurement technique which utilise the surface plasmon condition of thin metal surfaces, which can be used to measure small changes of refraction index with high sensitivity, e.g. as caused by the presence of biomolecules on the surface.

Ellipsometry—optical physical measurement technique which can be used to measure small changes of refraction index at surfaces with high sensitivity, by measuring changes in elliptisity of polarised light, e.g. as caused by the presence of biomolecules on the surface.

Piezoelectric crystal—crystal which frequency can be influenced by changes of mass or pressure which can be measured electrically, for example the change of mass caused by the presence of biomolecule(s), virus or cell(s) bound to the crystal surface.

Electrochemical electrode—measuring device which generates an electrical signal caused by an electrochemical reaction at the electrode which is related to a chemical parameter, e.g. pH, $pO_2$, $pCO_2$, the values of which can vary because of the presence of analyte(s) in a sample specific for a compound bound to the measuring device.

Thermistor—electrical resistance device which changes resistance with the temperature; biochemical reactions are characterised by e.g. specific values of heat consumption/formation, which can be registered via the thermistor.

A large amount of the carbohydrate sequences present in glycoproteins or in glycolipids, and usually also smaller fragments of these sequences, have shown biospecific binding to proteins, virus or cells.

The present invention describes a biosensor where this specificity is used for determination of such a component in a sample. The invention is characterised by that the carbohydrate or a derivative thereof is bound to a surface in the biosensor.

As carbohydrate, one can use fragments (oligosaccharides) of the carbohydrate sequences found in glycoproteins or in glycolipids and one can also use smaller fragments of these sequences, i.e. disaccharide, trisaccharide, tetrasaccharide or a pentasaccharide, because this size usually is sufficient for the oligosaccharide to bind a protein, virus or a cell in a biospecific manner. A review or such carbohydrate sequences can be found in e.g. Chemistry and Physics of Lipids, vol. 42, p. 153–172, 1986, and in Ann. Rev. Biochem., vol. 58, p. 309–350.

The oligosaccharide is usually modified in the reducing end with an aglycon, which is composed of a glycosidically bound organic group which is suitable for binding to the surface in the biosensor. Examples of aglycons are $OEtSEtCONHNH_2$,—$OEtSPhNH_2$, etc. The binding to the surface in the biosensor can be done directly or via a proteins, e.g. bovine serum albumine or via a chemical structure which has been adsorbed or which has been covalently bound to the surface. Such a chemical structure can contain reactive organic groups such as carboxyl-, sulfonate, cyanate, epoxy-, aldehyde groups or other groups suitable for chemical conjugation with for example an amine or thiol group in the aglycon.

More specific examples of analytes which can be analysed with biosensor according to the present invention are lectins, antibodies against carbohydrates, pathogenic virus or bacteria, such as urinary tract bacteria (e.g. P-fimbriated *E. coli*) or pathogens of the respiratory tract, and bacteria which cause infections/diarrhea in in gastrointestinal tract.

Non-limiting examples of carbohydrate structures of interest and which can be used in the form of a carbohydrate derivative in a biosensor according to the invention, are monosaccharides, disaccharides, trisaccharides and higher oligosaccharides which show biological activity or which has the ability to specifically bind one or more biomolecules or a group of biomolecules. Examples of biomolecules are other saccharides, peptides and proteins. Examples of such carbohydrate sequences are the blood group determinants (for example A, B, H, Lewis-a, Lewis-b, Lewis-x, Lewis-y), cancer-associated carbohydrate sequences, carbohydrate sequences (often di-, tri- or tetrasaccharides) which bind to pathogenic bacteria/toxins or virus of for example the respiratory, the gastrointestinal or the urinary tract, carbohydrate sequences which bind to proteins/cells/white blood cells associated with inflammatory reactions (for example selectin-carbohydrate reactions).

These and other carbohydrate structures which can be used in a biosensor according to the present invention often contain one or more of the following monosaccharides (or a derivative or an analog of any of these) which are α- or β-glycosidically bound: hexosamine, fucose, mannose, glucose, N-acetyl-glucosamine, N-acetyl-galactosamine, xylose, galactose, or another monosaccharide. These components are usually present in for example pyranose or furanose form.

Examples of carbohydrate derivatives are derivatives where the carbohydrate or a derivative or an analog, are modified in the reducing end with an O-, N-, C- or S-glycosidically bound aglycon which can be an aliphatic or an aromatic compound, an amino acid-, peptide- or protein molecule or a derivative thereof. The aglycon part can thus be composed of for example an O-, N-, C- or S-glycosidically bound aliphatic or aromatic compound which is bound to an amino acid-, peptide- or protein molecule or a derivative thereof. Examples of carbohydrate derivatives which can be used according to the invention are structures in which one or more of the hydroxyl groups in the carbohydrate, in addition to or instead of the hydroxyl group in the reducing end of the carbohydrate part, have been modified with an organic or inorganic group. This can be of interest, for example to increase/modify the biological activity or to facilitate the binding to the biosensor surface according to the invention.

The aglycon part or another group can be used for adsorption or covalent binding of the carbohydrate derivative to the surface of the biosensor and can be used in the invention as a spacer molecule between the biosensor surface and the carbohydrate part to minimise sterical hindrance in the binding of the analyte to the carbohydrate part in the biosensor according to the invention.

The aliphatic or aromatic compound in the aglycon can for example consist of structures of the type —R—X, where R— consists of an organic compound, for example an alkyl chain of the type (—$CH_2$)$_n$—, in which n is an integer, e.g. in the interval 2 to 8, or is composed of an aromatic group-containing structure, and where —X is for example a structure of the type —S—, amide (—NH—CO— or CO—NH—), amine (—NH—), a —N=N— group or another group suitable for binding to the surface in the biosensor or to a protein (i.e. in the latter case the carbohydrate derivative is a neoglycoprotein). When the carbohydrate derivative is a neoglycoprotein R can be used as a spacer between the protein part and the carbohydrate part. The spacer often has a functional part (—X— above) which has been used in the binding to the protein.

Suitable spacer and functional group is chosen by the person skilled in the art and does not limit the scope of the invention.

The carbohydrate derivative can also, according to the invention, be composed of a natural, in vitro isolated glycoprotein or a recombinant glycoprotein or a glycopeptide. This type of derivative can be adsorbed to the surface in the biosensor, for example a gold- or silica surface or another surface which adsorbs proteins, lipids or peptides.

In the case a covalent binding is desired one can, as in the case when the carbohydrate derivative is a neoglycoprotein, use for example the protein part's amino-, carboxyl-, or thiol groups for binding to the surface in the biosensor. This (as for the synthesis of the neoglycoprotein from carbohydrate spacer and protein) can be done with the standard techniques which normally are used for modification of proteins and for immobilisation of proteins to solid supports (see for example methods mentioned in Methods of Enzymology, volumes 44, 102, and 135), and the choice of suitable technology is made by the person skilled in the art in every specific case. Examples of methods are coupling or activation of carboxyl groups with carbodiimide reagents, N-hydroxysuccinimide reagents, of hydroxyl groups with CNBr, sulphonyl chloride (tresyl chloride, tosyl chloride), divinyl sulphone, periodate (gives aldehyde groups), thiol groups are activated with thiol reagents of the type N-succinionidyl 3-(2-pyridyldithio) propionate, etc.

As examples of surfaces according to the invention may be mentioned:

Carbohydrate-R—X-Biosensor surface or

Carbohydrate-R—X-Protein-Biosensor surface where Carbohydrate, R and X have been exemplified above. X and Protein can be directly adsorbed on the Biosensor surface above, but between X and Biosensor surface above and between Protein and Biosensor surface above can also a chemical group be present, for example a —CO—$CH_2CH_2$—S— group, i.e. for example:

Carbohydrate-R—NH—CO—$CH_2$—$CH_2$—S-Biosensor surface or

Carbohydrate-R—X-Protein-NH—CO—$CH_2$—$CH_2$—S-Biosensor surface.

As protein one can use for example bovine serum albumin, but all for the application suitable types of proteins can be used in the carbohydrate derivative-based biosensor according to the invention.

The biosensor according to the invention can be designed in a variety of configurations. Examples are:

a) planar carbohydrate surface which easily can be contacted with the sample, for example a surface designed as a dipstick, this surface can be placed in a measuring device for optical reflectance measurement in air.

b) Flow system with flow cell, the surface of which is modified with carbohydrate and where the signal is transferred with optical, electrochemical, thermical or gravimetric method and where the measuring device is placed in, or in close connection with the cell.

c) Cuvettte or other sample cell, which has been connected with a signal transducer equipped with carbohydrate to which the sample is added.

d) Planar carbohydrate surface which consists of part of the signal transducer which with ease can be brought into contact with the sample for a suitable time, whereafter the sample is removed and the surface of the signal transducer is characterised with a physical measuring method, for example electronic measurement, gravimetric measurement or thermal measurement.

In some situations, e.g. to increase the biosensor signal in the measurement of low concentrations of cells, it can be advantageous in the measurement of the analyte with the biosensor to add, after the binding of the analyte to the carbohydrate surface, microparticles modified with carbohydrate specific for the bound cell.

The surface of the biosensor can be, for example a gold surface or a modified gold surface, a plastic surface which has been modified with a gold surface, silver surface or another metallic surface, or modifications thereof with polymers to which chemical coupling of carbohydrate can be carried out.

Below are given non-limiting examples of carbohydrate surfaces which can be used in biosensors according to the invention for binding and analysis/determination of pathogenic bacteria of the urinary tract.

EXAMPLE

One example was performed as follows: Silica surface coated with a gold layer was modified with mercaptopropionic acid by dipping the surface in a 5 mM solution of the add. The carboxyl groups were modified with carbodiimide (EDC) for 2 hours, whereafter digalactoside with aglycon (Galα1-4Galβ—OEtSEtCONHNH$_2$), was coupled to the EDC-activated surface for 12 hours at pH 8.5 and the surface was then rinsed with buffer.

The thus obtained gold surface modified with digalactoside was dipped for 60 minutes (this time can be varied) in a sample with bacteria of the urinary tract (P-fimbriated *E. coli*) containing Galα1-4Gal-specific receptor protein, followed by rinsing of the surface with distilled water for 2 minutes. Another gold surface modified in the same way with Galα1-4Gal, was dipped in a sample containing another non-infectious *E. coli* strain which lack the Galα1-4Gal-specific receptor protein. The extent of binding of the different bacteria to the surfaces was compared with electrom microscopy. The bacteria with The Galα1-4Gal-receptor bound to the surface to a ca 10–15 times higher extent than the other bacteria. The binding of P-fimbriated *E. coli* to a gold surface modified with mercaptopropionic acid alone, was ca 20 times lower than to the Galα1-4Gal-modified surface.

Alternative non-limiting examples are given below in which a neoglycoprotein was bound covalently or adsorbed directly on a surface for use in biosensor according to the invention.

In procedure B, Galα1-4GalβOCH$_2$CH$_2$SCH$_2$CH$_2$C(O)—NHNH—BSA was coupled to the same type of EDC-activated gold plate as in the procedure above. The Galabiose-BSA derivative (0.1 mg/ml) was dissolved in 0.1 M boronate, pH 8.5 and EDC-activated plates were immersed in this solution for 1 hour. Subsequently the plates were immersed in a BSA solution (3 mg/ml in phosphate buffer for 1 minute and rinsed with buffer and distilled water and stored as above.

In procedure C, Gold plates (not pretreated with mercaptopropionic acid) were immersed in a solution of Galα1-4Galβ-BSA (0.1 mg/ml) in 0.1 M sodium phosphate, pH 6.0, for 1 hour and subsequently immersed in the above BSA solution (3 mg/ml) for 1 minute, rinsed with buffer and distilled water and stored as above.

These latter biosensor surfaces showed similar characteristics and low back-ground binding of bacteria as surface in the first example above.

What is claimed is:

1. An immobilized carbohydrate derivative biosensor, comprising:
    a surface,
    a binding group bound to the surface;
    an alkyl or aromatic organic spacer molecule bound to the binding group; and
    a carbohydrate derivative, O-, N-, C-, or S-glycosidically bound to the spacer molecule, which carbohydrate derivative specifically binds in a sample to at least one member selected from the group consisting of a protein, a virus and a cell.

2. The biosensor according to claim 1, wherein said carbohydrate derivative is a fragment of a naturally occurring carbohydrate sequence, which fragment binds in a biospecific manner to at least one member selected from the group consisting of a protein, a virus and a cell.

3. The biosensor according to claim 2, wherein the fragment of a naturally occurring carbohydrate sequence is a member selected from the group consisting of a mono-, di-, tri-, tetra-, or penta-saccharide sequence.

4. The biosensor according to claim 2, wherein the fragment of a naturally occurring carbohydrate sequence selectively binds to at least one member selected from the group consisting of a lectin, an antibody against a carbohydrate, a cancer cell, a protein associated with a blood group determinant, a pathogenic bacteria, a pathogenic virus, a pathogenic toxin, a protein associated with an inflammatory reaction, and a cell associated with an inflammatory reaction.

5. The biosensor according to claim 2, wherein the fragment of a naturally occurring carbohydrate sequence binds to P-fimbriated *E. coli*.

6. The biosensor according to claim 1, wherein said binding group is chemically bound or is bound via adsorption to the surface of the biosensor.

7. The biosensor according to claim 1, wherein said surface comprises a signal transducer.

8. The biosensor according to claim 7, wherein said signal transducer is a chemical transducer.

9. The biosensor according to claim 7, wherein said signal transducer is a physical transducer.

10. The biosensor according to claim 1, wherein said surface comprises a means for monitoring a physical signal.

11. The biosensor according to claim 10, wherein said means for monitoring a physical signal is at least one member selected from the group consisting of a photometer, a chemical electrode, an electrochemical electrode, a temperature signal transducer, and a pressure signal transducer.

12. The biosensor according to claim 1, wherein said carbohydrate derivative comprises at least one component selected from the group consisting of hexosamine-, fucose-, galactose-, glucose-, mannose-, xylose-, a N-acetylneuraminic acid residue, and analogs thereof.

13. The biosensor according to claim 12, wherein the carbohydrate derivative has been derivatized in at least one hydroxyl group or amino group thereof with an organic or inorganic group.

14. The biosensor according to claim 1, in which the carbohydrate derivative contains at least one O-, N-, S-, or C-glycosidically bound aglycon.

15. The biosensor according to claim 14, in which the aglycon contains at least one aliphatic or aromatic compound.

16. The biosensor according to claim 14, in which the aglycon part of the carbohydrate derivative contains an amino acid, peptide, or protein molecule.

17. The biosensor according to claim 1, in which the carbohydrate derivative comprises at least one of a glycoprotein and a neoglycoprotein.

18. The biosensor according to claim 1, wherein said surface is operably associated with an optical sensor which gives a signal change upon binding of a protein, a virus or a cell to the carbohydrate derivative bound via the spacer to the surface.

19. The biosensor according to claim 18, wherein the optical sensor functions by at least one method selected from the group consisting of surface plasmon changes, ellipsometry, reflection measurement and polarization measurement.

20. The biosensor according to claim 1, in which the surface is operably associated with a member selected from the group consisting of a piezoelectric crystal, an electrochemical electrode and a thermistor.

21. The biosensor according to claim 1, wherein said surface of the biosensor comprises gold.

22. A method of using the biosensor according to claim 1 to determine the presence or amount of a protein, a virus or a cell, comprising the steps of:
    exposing the biosensor to a sample containing a protein, a virus or a cell to be measured, binding a protein, virus or cell to the biosensor, and measuring the presence or amount of the protein, virus or cell in the sample.

23. The biosensor according to claim 1, wherein:

the spacer molecule comprises an alkyl chain of the type $(-CH_2)_n$, in which n is an integer from 2 to 8.

24. The biosensor according to claim 1, wherein:

the spacer molecule comprises an aromatic group-containing structure; and the binding group comprises a member selected from the group consisting of —S—, —NH—CO—, —CO—NH—, —NH—, and —N=N—.

25. The biosensor according to claim 1, wherein a chemical group is present between the surface and the binding group.

26. The biosensor according to claim 25, wherein the chemical group is a —CO—CH$_2$CH$_2$—S— group.

27. The immobilized carbohydrate derivative biosensor according to claim 1, further comprising a protein which is linked between the spacer molecule and the binding group.

28. The biosensor according to claim 27, wherein said carbohydrate derivative is a fragment of a naturally occurring carbohydrate sequence, which fragment binds in a biospecific manner to at least one member selected from the group consisting of a protein, a virus and a cell.

29. The biosensor according to claim 28, wherein the fragment of a naturally occurring carbohydrate sequence selectively binds to at least one member selected from the group consisting of a lectin, a cancer cell, a protein associated with a blood group determinant, a pathogenic bacteria, a pathogenic virus, a pathogenic toxin, a protein associated with an inflammatory reaction, and a cell associated with an inflammatory reaction.

30. The biosensor according to claim 28, wherein the fragment of a naturally occurring carbohydrate sequence is a member selected from the group consisting of a mono-, di-, tri-, tetra-, or penta-saccharide sequence.

31. The biosensor according to claim 27, wherein said surface comprises a signal transducer.

32. The biosensor according to claim 27, wherein said surface comprises a means for monitoring a physical signal.

33. The biosensor according to claim 32, wherein said means for monitoring a physical signal is at least one member selected from the group consisting of a photometer, a chemical electrode, an electrochemical electrode, a temperature signal transducer, and a pressure signal transducer.

34. The biosensor according to claim 27, wherein said surface is operably associated with an optical sensor which gives a signal change upon binding of a protein, a virus or a cell to the carbohydrate derivative.

35. The biosensor according to claim 34, wherein the optical sensor functions by at least one method selected from the group consisting of surface plasmon changes, ellipsometry, reflection measurement and polarization measurement.

36. The biosensor according to claim 27, in which the surface is operably associated with a member selected from the group consisting of a piezoelectric crystal, an electrochemical electrode and a thermistor.

37. The biosensor according to claim 27, wherein said surface of the biosensor comprises gold.

38. A method of using the biosensor according to claim 27 to determine the presence or amount of a protein, a virus or a cell, comprising the steps of:

exposing the biosensor to a sample containing a protein, a virus or a cell to be measured, binding a protein, virus or cell to the biosensor, and measuring the presence or amount of the protein, virus or cell in the sample.

39. The biosensor according to claim 27, wherein:

the spacer molecule comprises an alkyl chain of the type $(-CH_2)_n$, in which n is an integer from 2 to 8.

40. The biosensor according to claim 27, wherein:

the spacer molecule comprises an aromatic group-containing structure; and the binding group comprises a member selected from the group consisting of —S—, —NH—CO—, —CO—NH—, —NH—, and —N=N—.

41. The biosensor according to claim 27, wherein a chemical group is present between the surface and the binding group.

42. The biosensor according to claim 41, wherein the chemical group is a —CO—CH$_2$CH$_2$—S— group.

43. The biosensor according to claim 27, wherein the protein comprises bovine serum albumin.

44. The immobilized carbohydrate derivative biosensor according to claim 1, further comprising a protein which is linked between the binding group and the biosensor surface.

45. The biosensor according to claim 44, wherein said carbohydrate derivative is a fragment of a naturally occurring carbohydrate sequence, which fragment binds in a biospecific manner to at least one member selected from the group consisting of a protein, a virus and a cell.

46. The biosensor according to claim 45, wherein the fragment of a naturally occurring carbohydrate sequence is a member selected from the group consisting of a mono-, di-, tri-, tetra-, or penta-saccharide sequence.

47. The biosensor according to claim 45, wherein the fragment of a naturally occurring carbohydrate sequence selectively binds to at least one member selected from the group consisting of a lectin, a cancer cell, a protein associated with a blood group determinant, a pathogenic bacteria, a pathogenic virus, a pathogenic toxin, a protein associated with an inflammatory reaction, and a cell associated with an inflammatory reaction.

48. The biosensor according to claim 44, wherein said surface comprises a signal transducer.

49. The biosensor according to claim 44, wherein said surface comprises a means for monitoring a physical signal.

50. The biosensor according to claim 49, wherein said means for monitoring a physical signal is at least one member selected from the group consisting of a photometer, a chemical electrode, an electrochemical electrode, a temperature signal transducer, and a pressure signal transducer.

51. The biosensor according to claim 44, wherein said surface is operably associated with an optical sensor which gives a signal change upon binding of a protein, a virus or a cell to the carbohydrate derivative.

52. The biosensor according to claim 51, wherein the optical sensor functions by at least one method selected from the group consisting of surface plasmon changes, ellipsometry, reflection measurement and polarization measurement.

53. The biosensor according to claim 44, in which the surface is operably associated with a member selected from the group consisting of a piezoelectric crystal, an electrochemical electrode and a thermistor.

54. The biosensor according to claim 44, wherein said surface of the biosensor comprises gold.

55. A method of using the biosensor according to claim 44 to determine the presence or amount of a protein, a virus or a cell, comprising the steps of:

exposing the biosensor to a sample containing a protein, a virus or a cell to be measured, binding a protein, virus or cell to the biosensor, and measuring the presence or amount of the protein, virus or cell in the sample.

56. The biosensor according to claim 44, wherein:
the spacer molecule comprises an alkyl chain of the type ($-CH_2$)$_n$, in which n is an integer from 2 to 8.

57. The biosensor according to claim 44, wherein:
the spacer molecule comprises an aromatic group-containing structure; and
the binding group comprises a member selected from the group consisting of $-S-$, $-NH-CO-$, $-CO-NH-$, $-NH-$, and $-N=N-$.

58. The biosensor according to claim 44, wherein the protein comprises bovine serum albumin.

* * * * *